(12) United States Patent
Fallon (10) Patent No.: US 11,311,407 B1
(45) Date of Patent: Apr. 26, 2022

(54) BIDIRECTIONAL JAW DISPLACEMENT ORAL APPLIANCE

(71) Applicant: John M Fallon, Henderson, NV (US)

(72) Inventor: John M Fallon, Henderson, NV (US)

(73) Assignee: Apnea Sciences Corporation, Aliso Viejo, CA (US)

( * ) Notice: Subject to any disclaimer, the term of this patent is extended or adjusted under 35 U.S.C. 154(b) by 0 days.

(21) Appl. No.: 17/183,069

(22) Filed: Feb. 23, 2021

(51) Int. Cl.
*A61F 5/56* (2006.01)

(52) U.S. Cl.
CPC .................... *A61F 5/566* (2013.01)

(58) Field of Classification Search
CPC ...... A61F 5/56; A61F 5/566; A61F 2005/563; Y10S 602/902; A61C 7/08; A61C 7/36; A61C 7/10; A63B 71/085; A63B 2071/086; A63B 2071/0866
USPC ........ 128/848, 859, 861, 862; 433/6, 19, 24, 433/140
See application file for complete search history.

(56) References Cited

U.S. PATENT DOCUMENTS

| 8,833,374 | B2 | 9/2014 | Fallon et al. | |
| 10,849,783 | B2* | 12/2020 | Fallon | A61F 5/566 |
| 2011/0017220 | A1* | 1/2011 | Lindsay | A61F 5/566 |
| | | | | 128/848 |
| 2013/0263865 | A1* | 10/2013 | Khast | A61F 5/566 |
| | | | | 128/848 |

\* cited by examiner

*Primary Examiner* — Alireza Nia
*Assistant Examiner* — Robin Han
(74) *Attorney, Agent, or Firm* — Morland C. Fischer (57) ABSTRACT

Disclosed is a bidirectional jaw displacement oral appliance that is worn in the mouth of a user to reduce the effects of snoring and sleep apnea. The oral appliance includes an upper arch tray assembly against which the user's upper set of teeth are received and a lower arch tray assembly against which the user's lower set of teeth are received. An intermediate arch tray assembly is located between the upper and lower arch tray assemblies. The upper arch tray assembly is hingedly connected to the intermediate arch tray assembly so as to be rotatable with the user's upper set of teeth upwardly relative to the intermediate arch tray assembly. The lower arch tray assembly is adapted to move with the user's lower set of teeth in a horizontal direction relative to the upper and intermediate arch tray assemblies by which the user's lower jaw is advanced relative to the user's upper jaw to maintain an airway to the user's throat.

7 Claims, 7 Drawing Sheets

BIDIRECTIONAL JAW DISPLACEMENT ORAL APPLIANCE

BACKGROUND OF THE INVENTION

1. Field of the Invention

This invention relates to a bidirectional jaw displacement oral appliance to be worn in the mouth and over the teeth of a user during sleep to reduce the effects of snoring and/or sleep apnea. The jaw displacement oral appliance includes upper and lower arch tray assemblies within which the user's upper and lower sets of teeth are received and wherein the lower arch tray assembly is adapted to move horizontally (i.e., back and forth) with the user's lower set of teeth, and the upper arch tray assembly is adapted to rotate vertically (i.e., up and down) with the user's upper set of teeth relative to the lower arch tray assembly. By virtue of the foregoing, the upper arch tray assembly will remain in engagement with the user's upper set of teeth should the user open his mouth while asleep. Moreover, the position of the user's lower jaw can be adjusted forward of the upper jaw in order to maintain an open airway to the user's throat.

2. Background Art

Oral appliances are known to be inserted in the mouth and worn over the teeth of a user to maintain an open airway that runs through the appliance to the user's throat to improve the user's breathing during sleep. Examples of such oral appliances are available by referring to U.S. Pat. No. 8,833,374 issued Sep. 16, 2014 and U.S. Pat. No. 10,849,783 issued Dec. 1, 2020. The aforementioned patented oral appliances have particular application for use by those wishing to reduce the effects of snoring and/or sleep apnea. Each appliance includes upper and lower arch tray assemblies against which the user's upper and lower sets of teeth are seated during use. The lower arch tray assembly is slidably adjustable in a horizontal direction relative to the upper arch tray assembly to correspondingly advance the position of the user's lower jaw relative to the user's upper jaw in order to keep the aforementioned airway open to the user's throat as the user's condition changes over time.

Depending upon how the user sleeps and moves about, the position of the oral appliance could shift in the user's mouth relative to his upper and lower sets of teeth. In particular, if the user were to open his mouth while asleep, the upper arch tray assembly of the appliance could separate from the user's upper set of teeth. In that case, when the user closes his mouth, the appliance may be out of alignment with the user's upper set of teeth which could reduce the effectiveness of the appliance by no longer maintaining the user's lower jaw ahead of the upper jaw. In the case of U.S. Pat. No. 10,849,783 referred to above, the upper arch tray assembly is adapted to slide vertically (i.e., up and down) along a post relative to the lower arch tray assembly by which to enable the upper arch tray assembly of the oral appliance to continue to engage the user's upper set of teeth throughout the night whether the user's mouth is open or closed so that an open airway is maintained.

SUMMARY OF THE INVENTION

In general terms, a bidirectional jaw displacement oral appliance is disclosed to be worn in the mouth and over the teeth of a user during sleep to reduce the effects of snoring and/or sleep apnea. The oral appliance includes upper and lower arch tray assemblies and an intermediate arch tray assembly located therebetween. Each of the arch tray assemblies has an arcuate configuration with a curved front and a pair of sides lying opposite one another to match the bite pattern of the user's teeth. Each of the upper and lower arch tray assemblies includes a tooth impression liner within which the user's upper and lower sets of teeth are received during sleep.

Depending downwardly from the opposite sides of the arcuate upper arch tray assembly are a pair of pivoting couplers (e.g., hooks) that are received through respective coupler receiving openings formed in the opposite sides of the arcuate intermediate arch tray assembly. The upper and intermediate arch tray assemblies are pivotally connected together by means of the pivoting couplers so as to lie one above the other when the pivoting couplers carried by the upper arch tray assembly are pushed through the coupler receiving openings formed in the intermediate arch tray assembly. By virtue of the foregoing, when the user of the oral appliance opens and closes his mouth during sleep, the upper arch tray assembly will rotate at the pivoting couplers such that the closed front thereof moves up and down with the user's upper set of teeth in a generally vertical direction relative to the intermediate arch tray assembly. Accordingly, the user's upper set of teeth will remain engaged by and avoid becoming separated from the tooth impression liner of the upper arch tray assembly. In this case, the oral appliance will remain in alignment with the user's upper set of teeth so as to preserve the effectiveness of the appliance and thereby maintain the open airway to the user's throat.

A pair of position control blocks are located on top and at the opposite sides of the lower arch tray assembly for slidable receipt within respective locking channels that are formed on the bottom and at the opposite sides of the intermediate arch tray assembly. Each of the position adjustment blocks and the locking channels has a set of teeth which run along one side thereof to be moved into mating engagement with one another so as to hold the position adjustment blocks within the locking channels and thereby connect the intermediate arch tray to the lower arch tray assembly.

When it is desirable to move the lower arch tray assembly of the bidirectional jaw displacement oral appliance in a horizontal direction relative to each of the upper arch tray assembly and the intermediate arch tray assembly to which the upper arch tray assembly is coupled so that the user's lower jaw can be repositioned relative to the upper jaw, squeezing forces are momentarily applied to the opposite sides of the intermediate arch tray assembly. As a result of the squeezing forces, the intermediate arch tray assembly is momentarily compressed such that the teeth at one side of the locking channels thereof are moved out of their former mating engagement with the teeth at one side of the position adjustment blocks of the lower arch tray assembly. A pushing force is now applied to the lower arch tray assembly to cause the position control blocks to slide through the locking channels of the intermediate arch tray assembly so as to correspondingly adjust the location of the lower arch tray assembly and the user's lower jaw forward of the upper arch tray assembly and the user's upper jaw. Once the position of the lower arch tray assembly and the user's lower jaw has been adjusted as necessary to meet the needs of the user, the momentary squeezing forces being applied to the intermediate arch tray assembly are terminated. Accordingly, the intermediate arch tray assembly will now automatically expand back to its original shape, whereby the teeth of the locking channels will move back into their mating engagement with the teeth of the position adjustment blocks to once again hold the intermediate and lower arch tray assemblies in place one above the other.

DESCRIPTION OF THE PREFERRED EMBODIMENT

Turning to the drawings, details are provided of a bidirectional jaw displacement oral appliance 1 that is sized to fit within the mouth and over the teeth of a user so that the user's lower jaw can be selectively repositioned (i.e., advanced) by a variable distance in a horizontal direction relative to the user's upper jaw as is necessary to maintain an open airway to the user's throat in order to reduce the effects of snoring and sleep apnea when the user wears the oral appliance over his teeth while sleeping. What is more, the user's upper jaw can also be repositioned in a vertical upward direction relative to his lower jaw so as to minimize the likelihood that the user's upper set of teeth will pull out from the oral appliance in the event that the user opens his mouth wide while he is asleep wearing the oral appliance over his teeth. It may therefore be appreciated that the oral appliance 1 has application for use by one wishing to have an adjustable device to enable the user to cope with the effects of snoring and/or sleep apnea and minimize the chance that the oral appliance will become separated from the user's upper set of teeth which could negatively impact the efficacy of the appliance should the user's mouth be opened during sleep.

Referring concurrently to FIGS. 1-11 of the drawings, the bidirectional jaw displacement oral appliance 1 is shown including an upper arch tray assembly 3 and a lower arch tray assembly 5 that are held one above the other to create a continuous air path through the oral appliance to the user's throat. A flexible intermediate arch tray assembly 4 lies between the upper and lower arch tray assemblies 3 and 5. As will be disclosed in greater detail hereinafter, the upper, intermediate and lower arch tray assemblies 3-5 are coupled to one another such that the lower arch tray assembly 5 can be moved by the user relative to the upper arch tray assembly 3 back and forth in a horizontal direction. Likewise, the upper arch tray assembly 3 and the intermediate arch tray assembly 4 can be moved together relative to the lower arch tray assembly 5 up and down in a generally vertical direction.

In the case where the lower arch tray assembly 5 is moved as will be hereinafter described by the user in a horizontal direction, the user's lower jaw is correspondingly displaced relative to his upper jaw to enable the size of the air path to the user's throat to be selectively adjusted. In the case where the upper and the intermediate arch tray assemblies 3 and 4 move upwardly in a vertical direction, such as when the user opens his mouth during sleep, the user's upper set of teeth will also move upwardly with the upper arch tray assembly 3. As an important advantage of the present invention, should the user open his mouth wide, his upper set of teeth are likely to remain in engagement with the upper arch tray assembly 3 so that the horizontal position of the user's lower jaw relative to his upper jaw will be maintained throughout the night.

The upper arch tray assembly 3 of the bidirectional jaw displacement appliance 1 includes an upper tooth impression liner 9 and an upper liner receiving tray 10 that are preferably manufactured as a single piece by means of a 3-D printing process so that the tooth impression liner 9 is affixed to the top of the liner receiving tray 10. Each of the upper tooth impression liner 9 and the upper liner receiving tray 10 has a generally arcuate (i.e., curved) configuration to match the bite pattern of the user's set of teeth carried by his upper jaw.

The lower arch tray assembly 5 of the bidirectional jaw displacement appliance 1 includes a lower tooth impression liner 12 and a lower liner receiving tray 14 that are bonded together so that the liner receiving tray 14 is held in place on top of the lower tooth impression liner 12. In the alternative, the lower tooth impression liner 12 and the lower liner receiving tray 14 can also be manufactured as a single piece by means of a 3-D printing process. As in the case of the upper tooth impression liner 9 and the upper liner receiving tray 10, each of the lower tooth impression liner 12 and the lower liner receiving tray 14 has a generally arcuate (i.e., curved) configuration to match the bite pattern of the user's set of teeth carried by his lower jaw.

The intermediate arch tray assembly 4 includes a flexible coupler attachment tray 16 that is attached to the lower liner receiving tray 14 of the lower arch tray assembly 5 in a manner that will soon be described. The coupler attachment tray 16 of the intermediate arch tray assembly 4 also has a generally arcuate (i.e., curved) configuration to match the arcuate configuration of the upper and lower liner receiving trays 10 and 14 of the upper and lower arch tray assemblies 3 and 5.

As is shown in the drawings, each of the arcuate upper, intermediate and lower arch tray assemblies 3-5 of the oral appliance 1 as well as the upper and lower liner receiving trays 10 and 14 and the coupler attachment tray 16 thereof has a curved closed front end and a pair of opposite sides that are spaced from one another at an open rear end. An upper bite channel 18 (best shown in FIG. 2) runs around the top of the upper tooth impression liner 9 of the arcuate upper arch tray assembly 3. The upper bite channel 18 is sized to receive therewithin the upper set of teeth of the user carried by the user's upper jaw. A lower bite channel 20 (best shown in FIG. 4) runs around the bottom of the lower tooth impression liner 12 of the arcuate lower arch tray assembly 5. The lower bite channel 20 is sized to receive therewithin the lower set of teeth of the user carried by the user's lower jaw.

Figure 1:
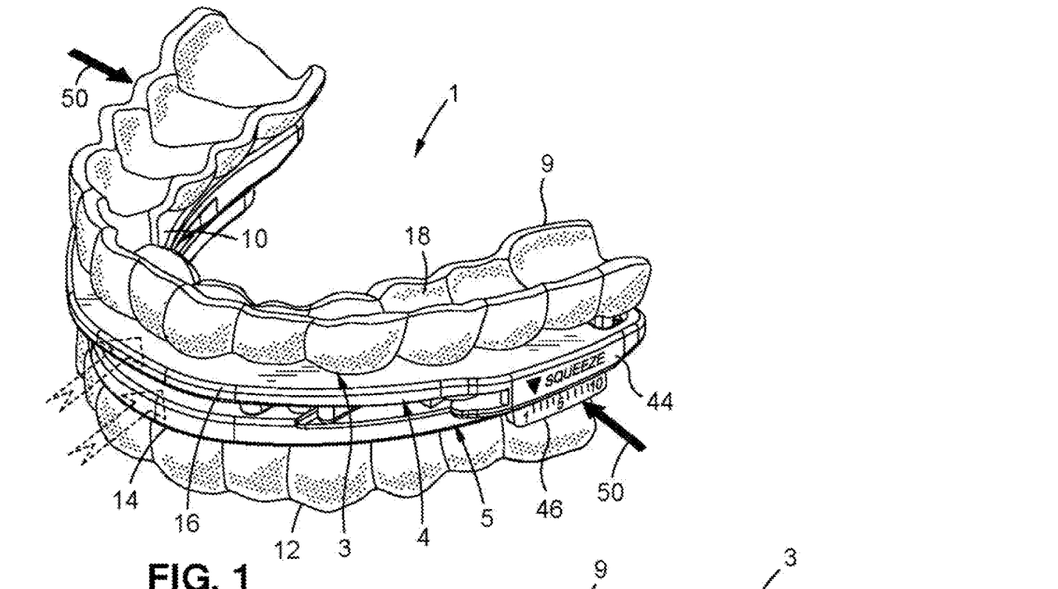
FIG. 1 is a perspective view of a bidirectional jaw displacement oral appliance according to a preferred embodiment of this invention.
Figure 2:
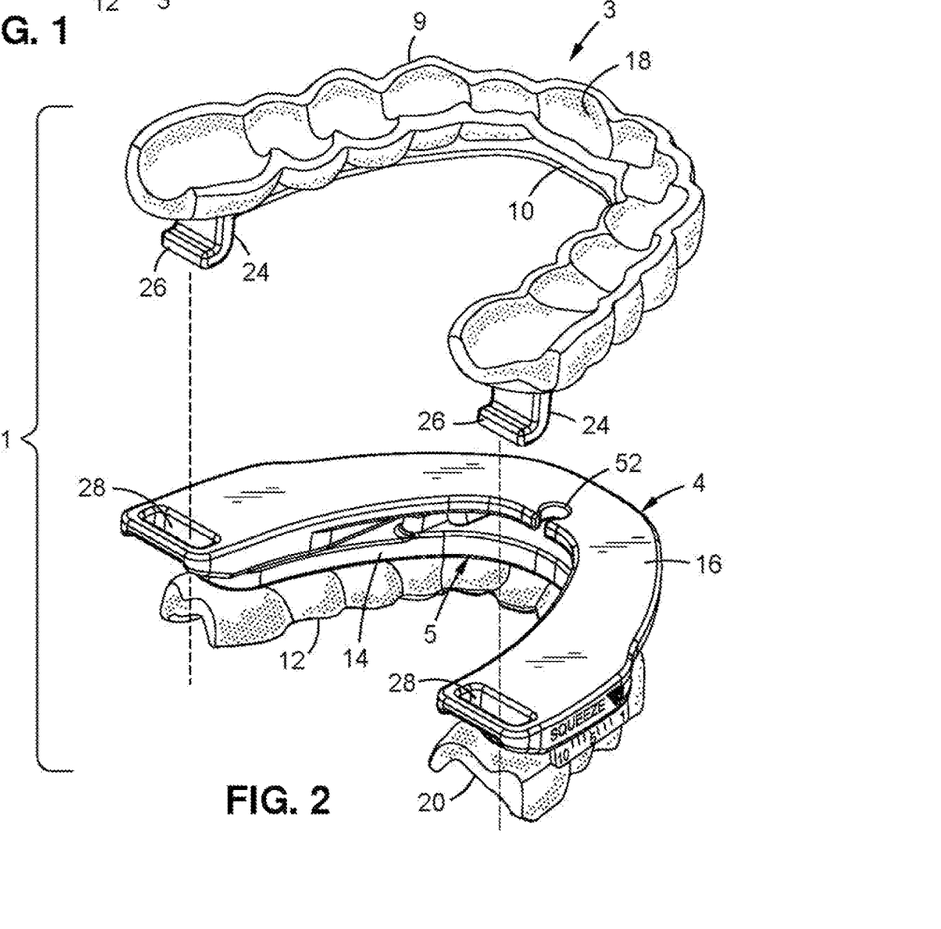
FIG. 2 is an exploded view of the jaw displacement oral appliance of FIG. 1.
Figure 3:
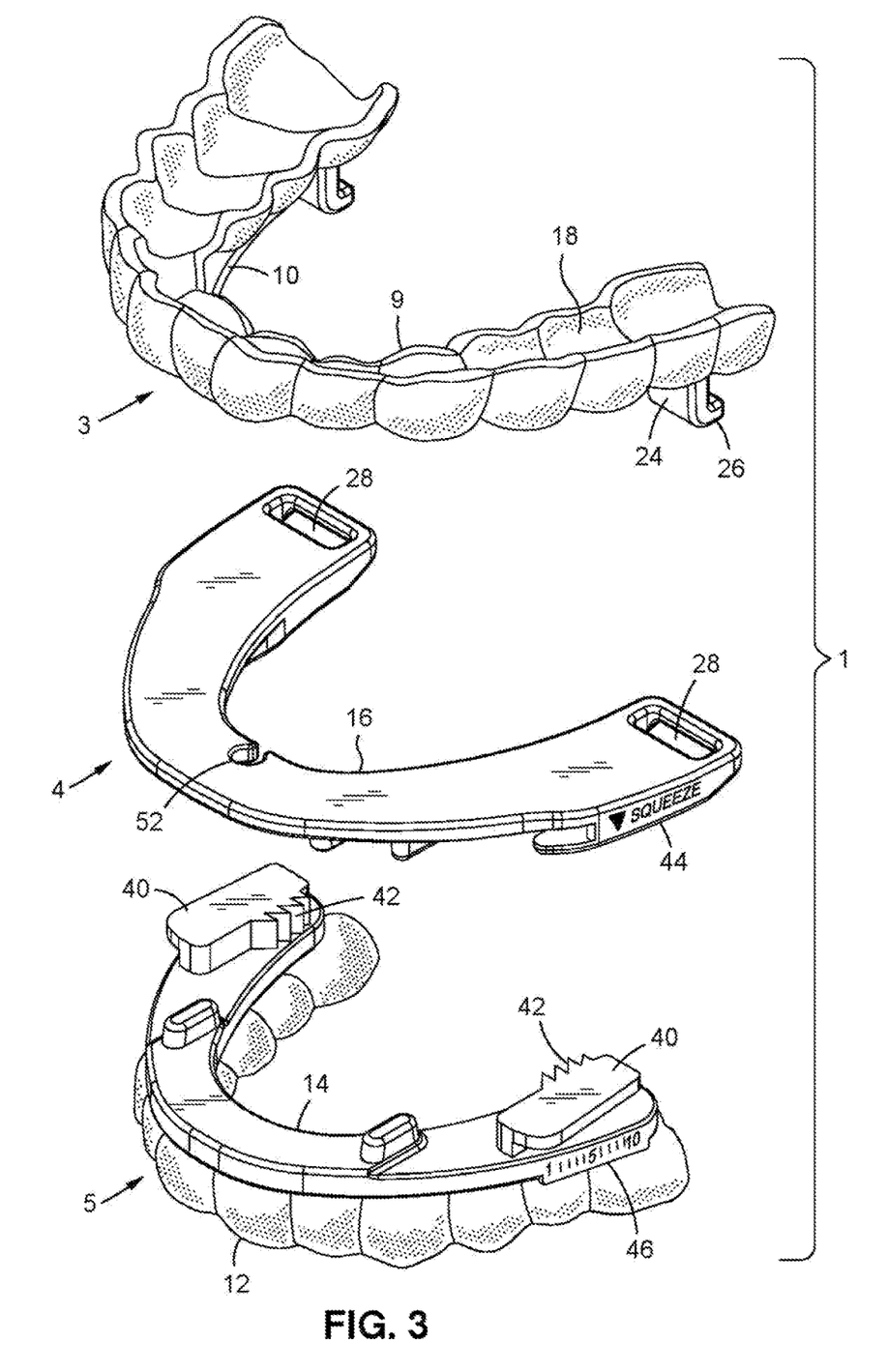
FIG. 3 is an exploded top view showing upper, lower and intermediate arch tray assemblies of the jaw displacement oral appliance of FIG. 1.

As an important feature of the bidirectional jaw displacement appliance 1, a pair of pivoting couplers 24 are coextensively connected to and depend downwardly from the opposite sides of the arcuate upper liner receiving tray 10 at the open rear end of the upper arch tray assembly 3. In a preferred embodiment, each pivoting coupler 24 has the L-shape of a hook. However, the pivoting couplers 24 can have other suitable shapes such as, for example, that of a post. A stop 26 turns outwardly from the bottom of each pivoting coupler 24. As is best shown in FIG. 3, a pair of coupler receiving openings or slots 28 are formed in the opposite sides of the arcuate coupler attachment tray 16 at the open rear end of the intermediate arch tray assembly 4.

Figure 5:
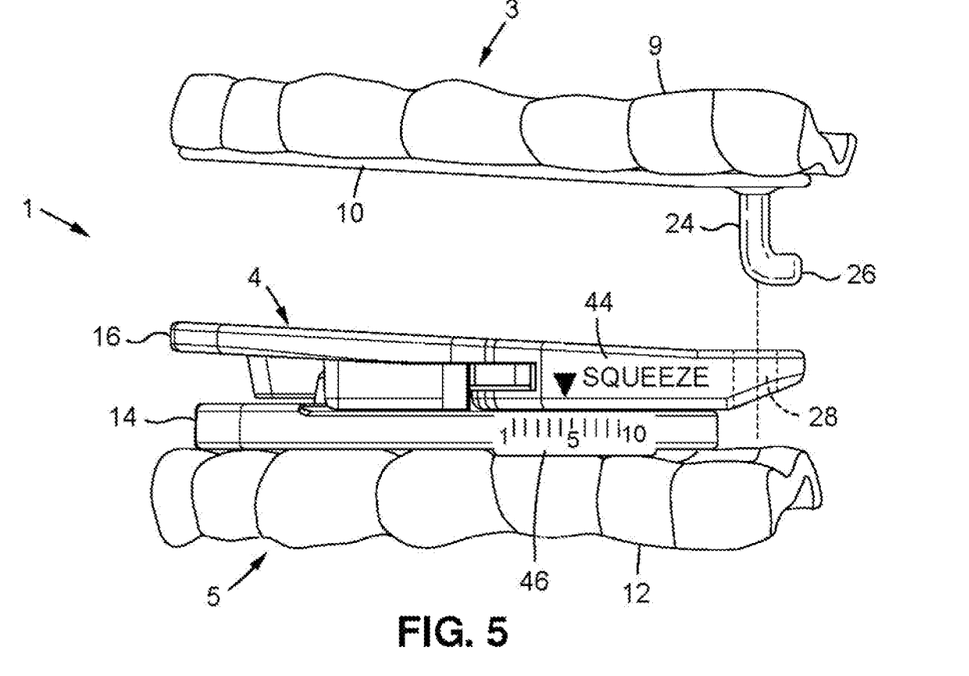
FIG. 5 shows the upper arch tray assembly of the jaw displacement oral appliance being pivotally coupled to the intermediate arch tray assembly by means of a pair of couplers depending downwardly from the upper arch tray assembly.
Figure 6:
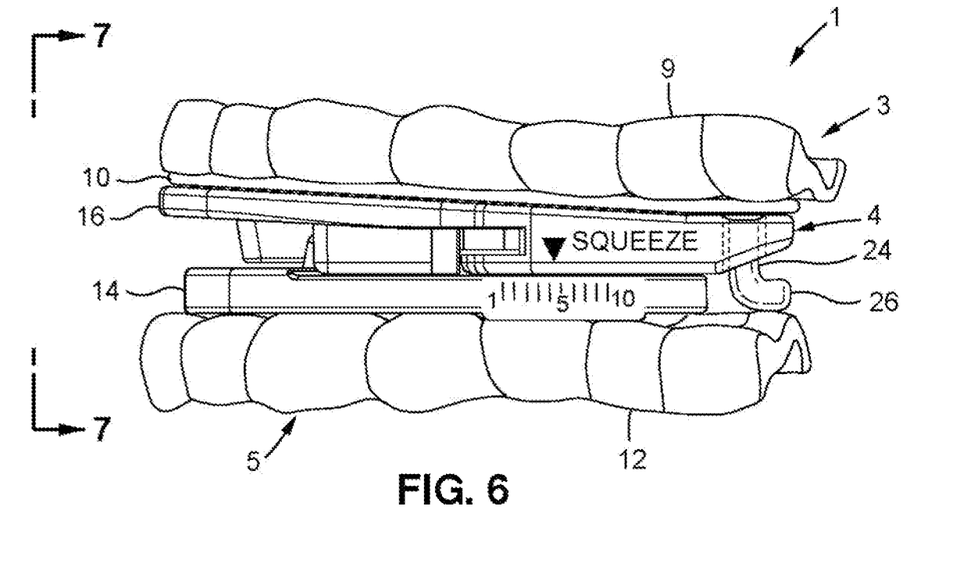
FIG. 6 shows the upper and intermediate arch tray assemblies of the jaw displacement oral appliance after being coupled one above the other.

As is best shown in FIG. 5, the pivoting couplers 24 that depend downwardly from the upper liner receiving tray 10 of the upper arch tray assembly 3 are axially aligned with respective ones of the coupler receiving openings 28 formed in the coupler attachment tray 16 of the intermediate arch tray assembly 4. The upper and intermediate arch tray assemblies 3 and 4 are coupled together one above the other when the pivoting couplers 24 are pushed through the coupler receiving openings 28 such that the upper arch tray assembly 3 can ride up and down relative to the intermediate arch tray assembly 4 over and along the pivoting couplers 24. The stops 26 that turn outwardly from the bottoms of the pivoting couplers 24 prevent the withdrawal of the pivoting couplers 24 from the coupler receiving openings 28 to block the separation of the upper and intermediate arch tray assemblies 3 and 4 from one another.

Figure 9:
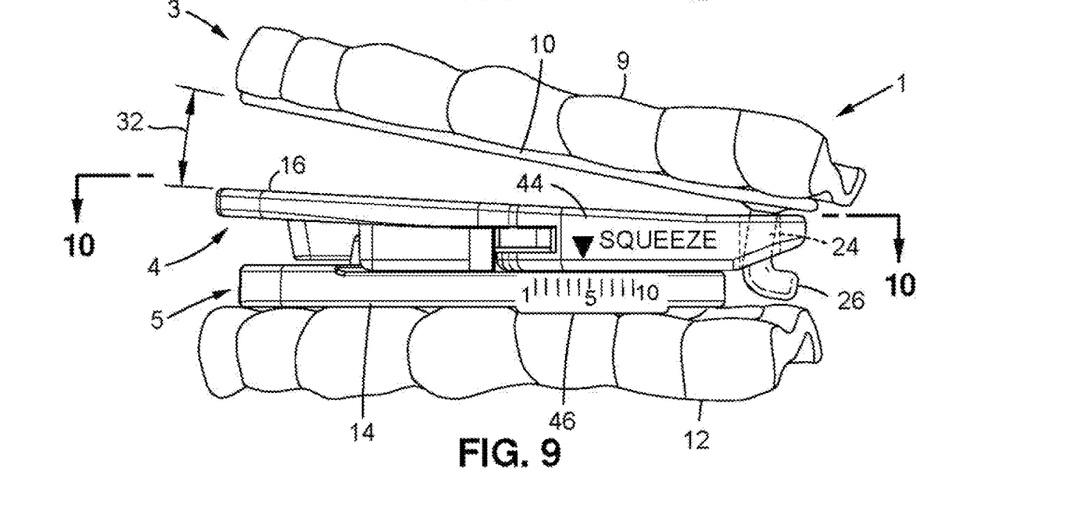
FIG. 9 shows the jaw displacement oral appliance when the user's mouth is opened and the upper arch tray assembly rotates upwardly relative to the intermediate arch tray assembly.
Figure 10:
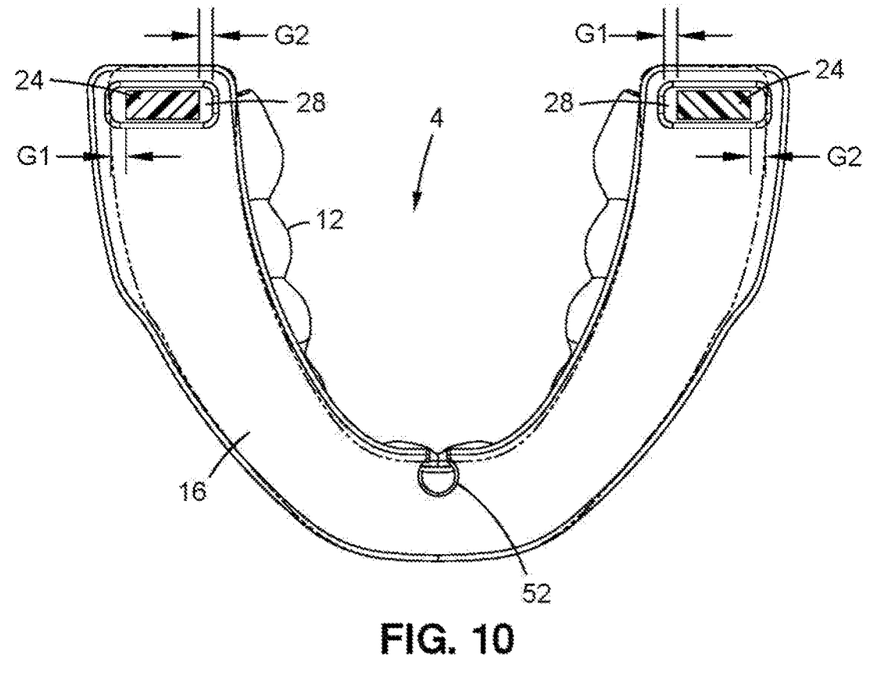
FIGS. 10 and 11 show the pair of couplers of the upper arch tray assembly slidably received within coupler receiving openings formed in the intermediate arch tray assembly when viewed in the direction of lines 10-10 of FIG. 9.
Figure 11:
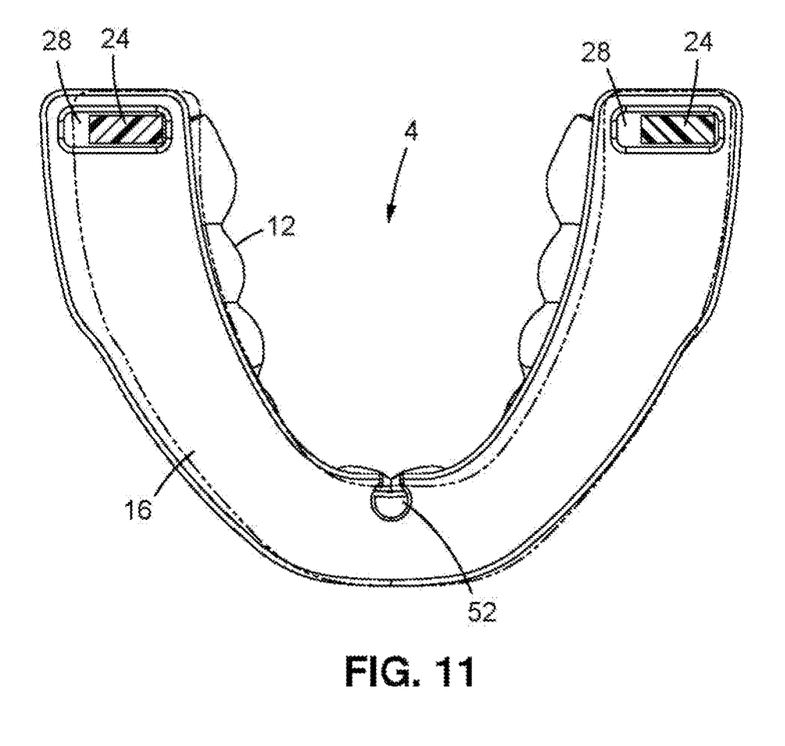

As is best shown in FIGS. 10 and 11, the coupler receiving openings 28 that are formed in the coupler attachment tray 16 of the intermediate arch tray assembly 4 are longer than the cross section of the pivoting couplers 24 that are received through the openings 28. Therefore, as is best shown in FIG. 9, the pair of pivoting couplers 24 are adapted to rock back and forth (i.e., pivot) within their coupler receiving openings 28. It may be appreciated that the pivoting couplers 28 function as hinges at which to enable the upper tray assembly 3 from which the couplers 28 depend to rotate up and down in a generally vertical direction relative to the intermediate arch tray assembly 4 so as to move upwardly and away from the lower arch tray assembly 5 and the user's lower set of teeth.

What is more, because the coupler receiving openings 28 are longer than the cross section of the couplers 24, gaps (designated G1 and G2 in FIG. 10) are established within the openings 28 at each side of the couplers 24. The gaps allow the pivoting couplers 24 to slide laterally back and forth through the openings 28 (best shown in FIG. 11) to compensate for both medial and lateral movements of the user's upper jaw that are transferred to the couplers 24 when the user wears the oral appliance 1 and opens his mouth while asleep so as to further reduce the chance that the user's upper set of teeth will fall out of the upper arch tray assembly 3.

Figure 7:
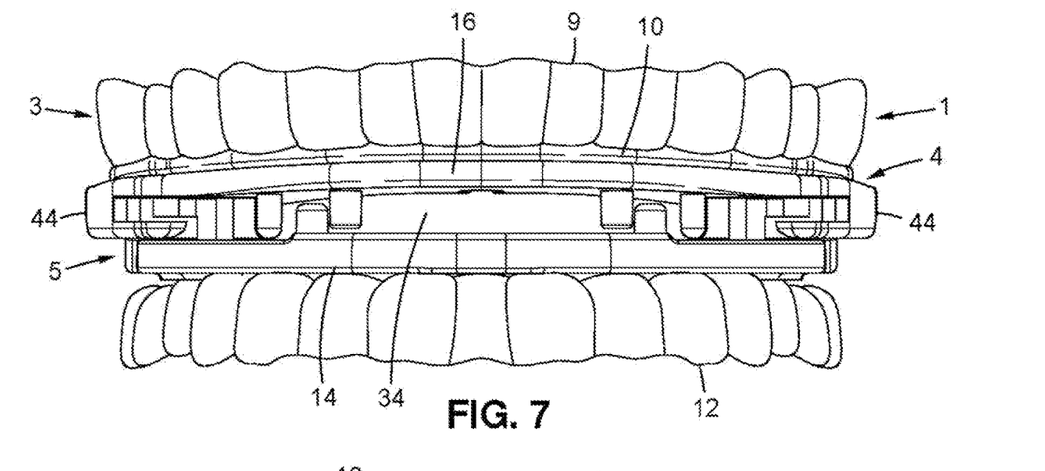
FIG. 7 is a front view of the jaw displacement oral appliance when viewed in the direction of lines 7-7 of FIG. 6.
Figure 8:
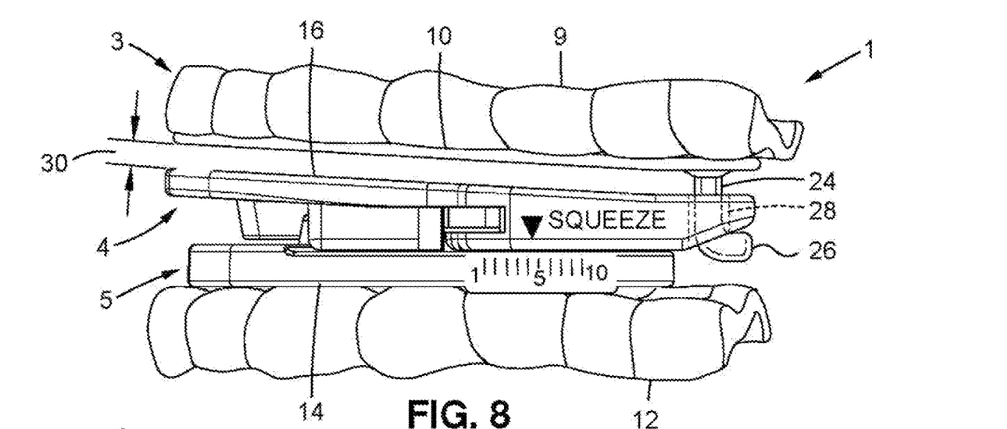
FIG. 8 shows the jaw displacement oral appliance at rest when a user's mouth is closed and the upper arch tray assembly lays on top of the intermediate arch tray assembly.

In this same regard, FIGS. 7 and 8 show the bidirectional jaw displacement oral appliance 1 at rest as it would appear while being worn by a user who is asleep with his upper set of teeth located in the upper tooth impression liner 9 of the upper arch tray assembly 3 and his lower set of teeth located in the lower tooth impression liner 12 of the lower arch tray assembly 5. In this case, the user's mouth is closed, such that the upper arch tray assembly 3 lays on top and is separated from the intermediate arch tray assembly 4 by a relatively short distance designated by reference numeral 30 in FIG. 8.

FIG. 9 shows the bidirectional jaw displacement oral appliance 1 covering the user's teeth when he opens his mouth while asleep. Because the open rear end of the arcuate upper arch tray assembly 3 is hingedly connected to the open rear end of the arcuate coupler attachment tray 16 of the intermediate arch tray assembly 4 by means of the pivoting couplers 24 that extend therebetween, and depending upon how wide the user's mouth is opened, the closed front end of the upper arch tray assembly 3 rotates upwardly together with the user's upper set of teeth through an angle of about 30-45 degrees. Accordingly, the upper arch tray assembly 3 now moves away from the intermediate arch tray assembly 4 to increase the separation therebetween by a longer distance designated by reference numeral 32 in FIG. 9. By virtue of the foregoing, and as was explained above, the user's upper set of teeth are less likely to separate from the upper bite channel 18 (of FIG. 3) of the upper tooth impression liner 9 of the upper arch tray assembly 3 that could otherwise cause the oral appliance 1 to separate from the user's upper set of teeth and affect the position of the user's lower jaw relative to his upper jaw as the user's mouth is repeatedly opened and closed throughout the night.

Figure 4:
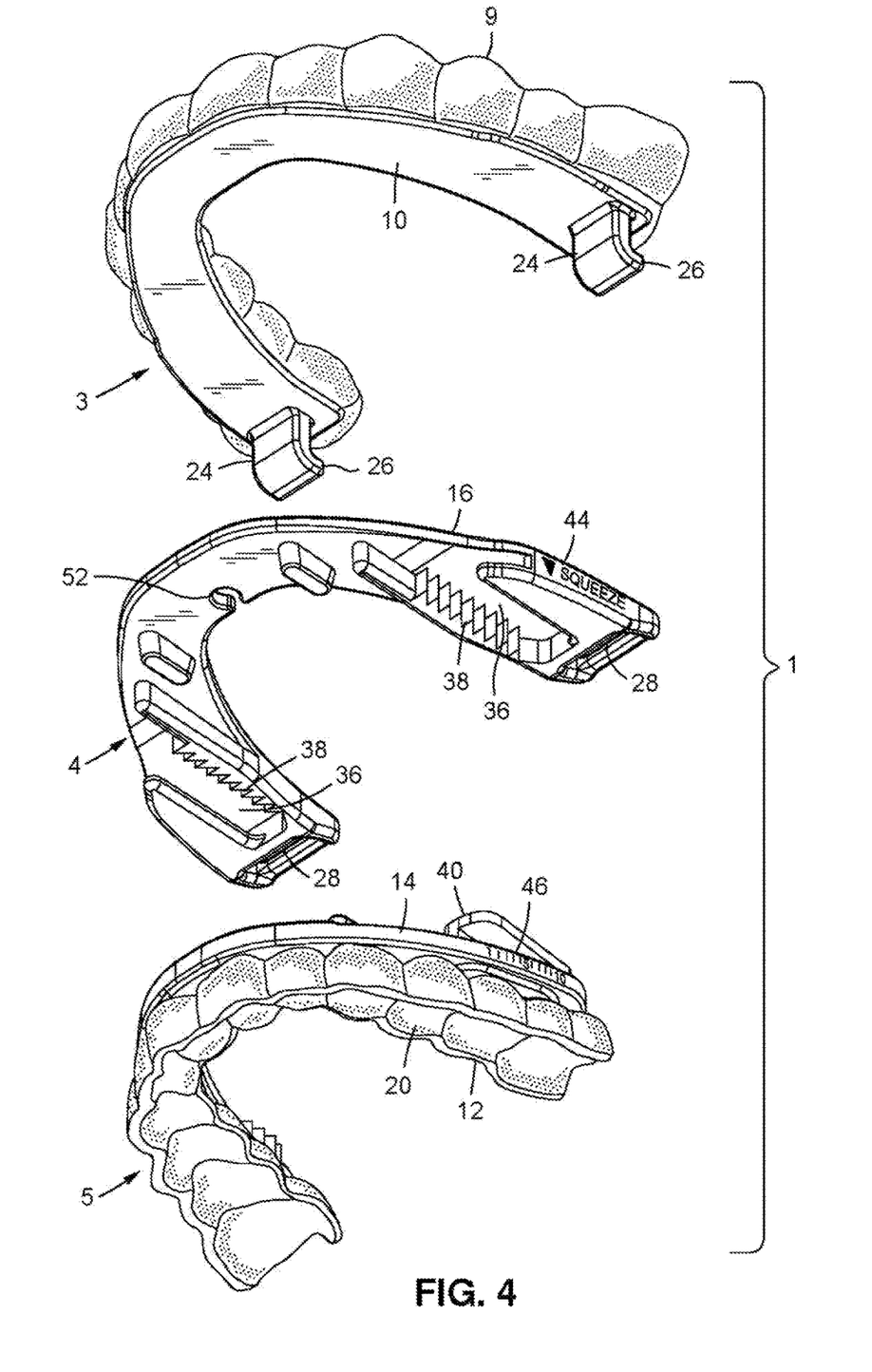
FIG. 4 is an exploded bottom view showing the upper, lower and intermediate arch tray assemblies of the jaw displacement oral appliance of FIG. 3.

Referring to FIGS. 3 and 4, details are provided of the means by which the intermediate arch tray assembly 4 of the bidirectional jaw displacement oral appliance 1 is coupled to the lower arch tray assembly 5 such that the intermediate and lower arch tray assemblies 4 and 5 as well as the user's lower jaw and the user's lower set of teeth that are located in the lower bite channel 20 of the lower tooth impression liner 12 can be moved with one another back and forth relative to the upper arch tray assembly 3 as well as the user's upper jaw and the user's upper set of teeth that are located in the upper bite channel 18 of the upper tooth impression liner 9. By virtue of the foregoing, the position of the user's lower jaw can be selectively adjusted along a horizontal direction relative to the position of the user's upper jaw to correspondingly adjust the horizontal advancement of the lower jaw and the size of the air path (designated 34 in FIG. 7) that runs to the user's throat.

As is best shown in FIG. 4, a recessed locking channel 36 is formed (e.g., molded) into the bottom and at each side of the arcuate coupler attachment tray 16 of the intermediate arch tray assembly 4. The locking channels 36 run parallel to one another. A row of teeth 38 is formed (e.g., molded) along one side of each locking channel 36. As is best shown in FIG. 3, located at opposite sides of and standing upwardly from the top of the arcuate lower liner receiving tray 14 of the lower arch tray assembly 5 are a pair of position adjustment blocks 40. A row of teeth 42 is formed (e.g., molded) along one side of each position control block 40.

During the assembly of the bidirectional jaw displacement oral appliance 1, the lower liner receiving tray 14 of the lower arch tray assembly 3 is mounted against the bottom of the coupler attachment tray 16 of the intermediate arch tray assembly 4. To accomplish the foregoing, the pair of position adjustment blocks 40 which stand upwardly from the lower liner receiving tray 14 are pushing into slidable receipt by respective ones of the pair of locking channels 36 that are formed in the bottom of the coupler attachment tray 16, whereby the opposing trays 14 and 16 of the intermediate and lower arch tray assemblies 4 and 5 are coupled together and held in place one over the other. In this same regard, the rows of teeth 42 which run along one side of the pair of upstanding position adjustment blocks 40 are moved into releasable locking engagement with and mesh against the rows of teeth 38 which run along one side of the pair of recessed locking channels 36. However, it may be appreciated that any suitable interlocking ratchet means may be substituted for the opposing rows of teeth 38 and 42.

By virtue of the foregoing, the user is provided with the ability to release the locking meshing engagement of the teeth 42 of the position adjustment blocks 40 with the teeth 38 of the locking channels 36. That is, the position of the lower arch tray assembly 5 that engages the user's lower jaw can be selectively changed along a horizontal direction relative to the upper and the intermediate arch tray assemblies 3 and 4 that are coupled to one another by the pivoting couplers 24 and engage the user's upper jaw.

A pair of position control pads 44 are located at and molded into opposite sides of the coupler attachment tray 16 of the intermediate arch tray assembly 4. A position indication scale 46 is molded into or printed on each side of the lower liner receiving tray 14 of the lower arch tray assembly 5 so as to lie below a position control pad 44. The coupler attachment tray 16 of the flexible intermediate arch tray assembly 4 is responsive to momentary compressive squeezing forces represented by the directional arrows 50 in FIG. 1 that are simultaneously applied towards one another at the position control pads 44 to temporarily compress and change the shape of the coupler attachment tray 16, whereby the opposite sides of the tray 16 are squeezed together. At the same time, the teeth 38 of the locking channels 36 at the bottom of the coupler attachment tray 16 are temporarily moved out of their former locking engagement with the teeth 42 formed in the position adjustment blocks 40 at the top of the lower liner receiving tray 14. A keyhole notch 52 is formed in the coupler attachment tray 16 of the intermediate arch tray assembly 4 midway around the curved front end thereof to facilitate an even compression of the opposite sides towards one another in response to the squeezing forces applied thereto.

The user can now apply a pushing (or pulling) force to change the position of the lower arch tray assembly 5 and thereby advance the user's lower jaw in the horizontal direction. Because the coupler attachment tray 16 of the intermediate arch tray assembly 4 is coupled to the upper liner receiving tray 10 of the upper arch tray assembly 3 by means of the pair of pivoting couplers 24 which depend from tray 10 for receipt through the coupler receiving openings 28, the lower arch tray assembly 5 is displaced relative to both the upper and intermediate arch tray assemblies 3 and 4. By changing the position of the lower arch tray assembly 3 in a horizontal direction relative to the upper liner receiving tray 10 of the upper arch tray assembly 3, the position of the user's lower jaw is correspondingly moved forwards or backwards relative to his upper jaw to vary the size of the air path 34 (of FIG. 7) to the user's throat as may be necessary over time.

After the position of the lower arch tray assembly 5 has been adjusted relative to the position of the upper liner receiving tray 10 of the upper arch tray assembly 3, the momentary compressive squeezing forces 50 are terminated. Accordingly, the formerly compressed coupler attachment tray 16 of the intermediate arch tray assembly 4 will automatically expand back to its initial arcuate shape. At the same time, the teeth 38 of the locking channels 36 will move back into their mating interlocking engagement with the opposing teeth 42 of the position adjustment blocks 40 so that the intermediate and lower arch tray assemblies 4 and 5 will once again be held in place connected one above the other. The location of the position control pads 44 above the position indication scale 46 provides the user with a visual indication of the position of the lower arch tray assembly 5 with respect to the upper and the intermediate arch tray assemblies 3 and 4 so that the user can make regular controllable and precise horizontal position adjustments of the lower arch tray assembly 5 to correspondingly change the position of his lower jaw relative to his upper jaw.

It has just been described herein that the lower arch tray assembly 5 is moved in a horizontal direction relative to the upper arch tray assembly 3 once compressive squeezing forces have been applied to the position control pads 44 at opposite sides of the coupler attachment tray 16 of the intermediate arch tray assembly 4. However, it is to be expressly understood that, in the alternative, the upper arch tray assembly 3 can be grasped and moved in the same horizontal direction relative to the lower arch tray assembly 5 after the coupler attachment tray 16 is first compressed. In this case, the user's upper jaw will be positioned forwards and backwards relative to the user's lower jaw.

Figure 12:
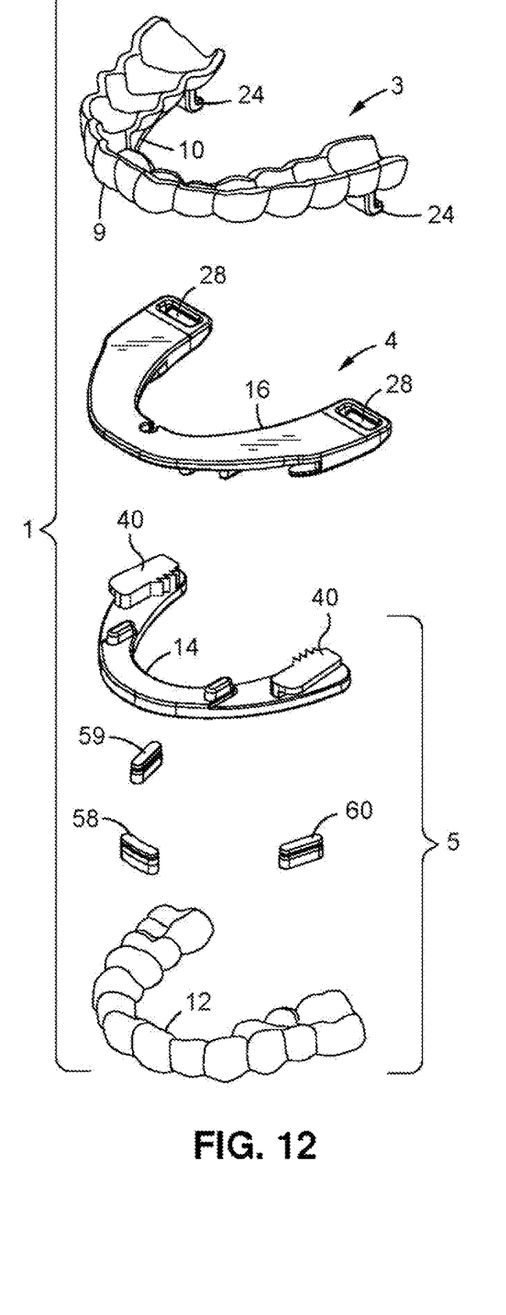
FIGS. 12 and 13 are top and bottom exploded views to illustrate an alignment feature of the jaw displacement oral appliance.
Figure 13:
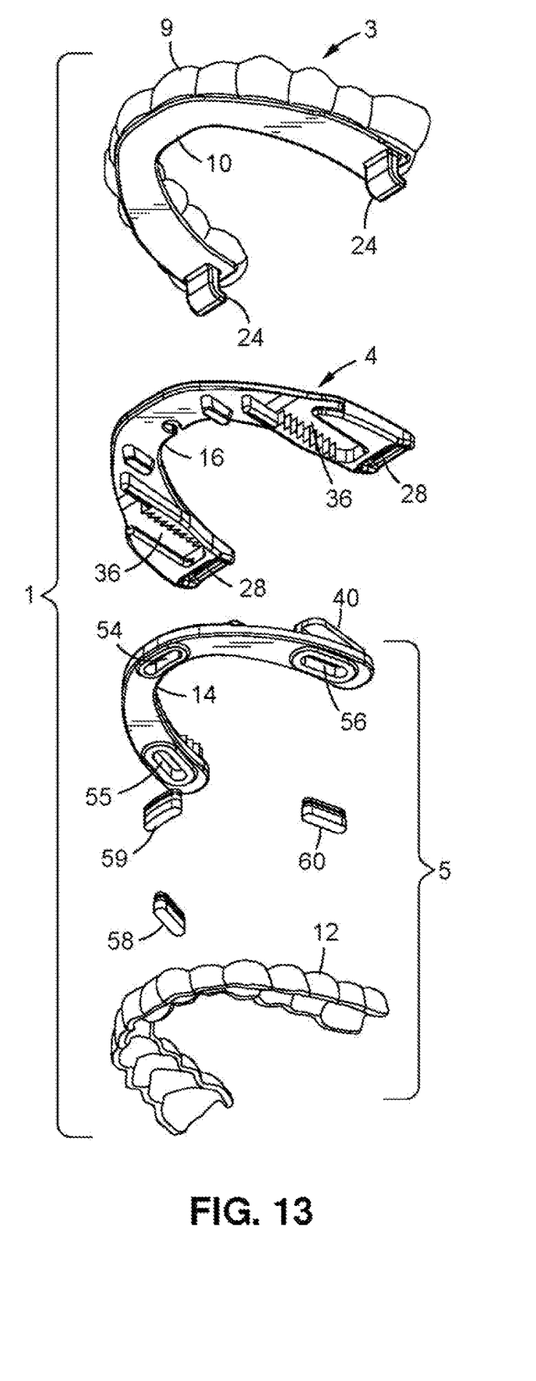

Referring now to FIGS. 12 and 13 of the drawings, the bidirectional jaw displacement oral appliance 1 is shown with an alignment feature that enables the arcuate upper liner receiving tray 10 of the upper arch tray assembly 3 to be accurately positioned with respect to the arcuate coupler attachment tray 16 of the intermediate arch tray assembly 4 and the arcuate lower liner receiving tray 14 of the lower arch tray assembly 5 during the assembly of the oral appliance. More particularly, alignment pockets 54, 55 and 56 (best shown in FIG. 13) are formed (e.g., molded) in the bottom of the lower liner receiving tray 14 at the front and opposite sides thereof. Alignment pegs 58, 59 and 60 are coextensively connected (e.g., by means of a 3-D printing process) to the top of the lower tooth impression liner 12 at the front and opposite sides thereof.

The alignment pegs 58-60 are axially aligned with the alignment pockets 54-56 so that the pegs 58-60 at the top of the lower tooth impression liner 12 are press fit within respective ones of the pockets 54-56 at the bottom of the lower liner receiving tray 14. The position adjustment blocks 40 at the top of the lower liner receiving tray 14 are slidably received by the toothed locking channels 36 at the bottom of the coupler attachment tray 16. The pivoting couplers 24 of the upper liner receiving tray 10 are pushed through the coupler receiving openings 28 of the coupler attachment tray 16. Accordingly, the arcuate upper, intermediate and lower arch tray assemblies 3-5 will be aligned one above the other to be packaged and shipped to the user of the oral appliance 1.

The invention claimed is:

1. A jaw displacement oral appliance to be inserted in the mouth of a user to adjust the position of the user's lower jaw relative to the user's upper jaw so as to maintain an open airway to the user's throat through which the user can breathe while sleeping, said oral appliance comprising:
   an upper arch tray assembly having an upper tooth impression liner configured to receive an upper set of teeth of the user's tipper jaw during sleep;

a lower arch tray assembly having a lower tooth impression liner configured to receive the a lower set of teeth of the user's lower jaw during sleep;

an intermediate arch tray assembly lying between said upper and said lower arch tray assemblies and being attached to said lower arch tray assembly, and each of said upper, said intermediate and said lower arch tray assemblies having a pair of sides that are spaced from and lie opposite one another;

a coupler connected to and extending downwardly from each of the pair of sides of said upper arch tray assembly and being pivotally coupled to respective ones of the pair of sides of said intermediate arch tray assembly, whereby said upper and said intermediate arch tray assemblies are pivotally connected together and said upper arch tray assembly is rotatable at said couplers with the user's upper set of teeth upwardly relative to said intermediate arch tray assembly so as to pivot away from said lower arch tray assembly and the user's lower set of teeth when the user's mouth is opened during sleep;

a coupler receiving opening formed in each of the pair of sides of said intermediate arch tray assembly such that the couplers that extend downwardly from the pair of sides of said upper tray assembly are received through respective one of the coupler receiving openings formed in the pair of sides of said intermediate arch tray assembly, whereby said upper and said intermediate arch tray assemblies are pivotally connected together and said upper arch tray assembly is rotatable at said couplers with the user's upper set of teeth upwardly relative to said intermediate arch tray assembly so as to pivot away from said lower arch tray assembly; and wherein said lower arch tray assembly is attached to said intermediate arch tray assembly such that said lower arch tray assembly is adapted to move with the user's lower set of teeth in a horizontal direction relative to each of said intermediate arch tray assembly and said upper arch tray assembly that is pivotally connected to said intermediate arch tray assembly, whereby to correspondingly adjust the position of the user's lower jaw relative to the position of the user's upper jaw.

2. The jaw displacement oral appliance recited in claim 1, wherein each of said upper, said intermediate and said lower arch tray assemblies has an arcuate configuration with a curved front that matches a bite pattern of the user's upper and lower sets of teeth.

3. The jaw displacement oral appliance recited in claim 1, wherein said couplers that extend downwardly from the pair of sides of said upper tray assembly for receipt through the respective ones of said coupler receiving openings formed in the pair of sides of said intermediate arch tray assembly have an L-shape.

4. The jaw displacement oral appliance recited in claim 1, wherein said coupler receiving openings formed in the pair of sides of said intermediate arch tray assembly are longer than the cross section of said couplers that are received through the respective ones of said coupler receiving openings, such that said couplers are slidable late rally through said coupler receiving openings.

5. The jaw displacement oral appliance recited in claim 1, wherein said lower arch tray assembly has a position adjustment block located at each of the pair of sides thereof and said intermediate arch tray assembly has a locking channel located at each of the pair of sides thereof, said position adjustment blocks being received within and slidable through respective ones of said locking channels when said lower arch tray assembly moves in said horizontal direction relative to each of said intermediate arch tray assembly and said upper arch tray assembly that is pivotally connected to said intermediate arch tray assembly.

6. The jaw advancement oral appliance recited in claim 5, wherein each position adjustment block and each locking channel that is located at each of the sides of the lower and the intermediate arch tray assemblies has a set of teeth, the sets of teeth of said position adjustment blocks and said locking channels lying in meshing engagement with one another, whereby said lower arch tray assembly and said intermediate arch tray assembly are mated in releasable locking engagement with one another.

7. The jaw advancement oral appliance recited in claim 6, wherein said intermediate arch tray assembly is responsive to compressive forces being simultaneously applied to the pair of sides thereof to compress said intermediate arch tray assembly and thereby move the sets of teeth of said locking channels out of their meshing engagement with the sets of teeth of the position adjustment blocks to enable said position adjustment blocks to slide through said locking channels and said lower arch tray assembly to move in said horizontal direction relative to each of said intermediate arch tray assembly and said upper arch tray assembly that is pivotally connected to said intermediate arch tray assembly.

* * * * *